US006577708B2

(12) United States Patent
Chapman et al.

(10) Patent No.: US 6,577,708 B2
(45) Date of Patent: Jun. 10, 2003

(54) DIFFRACTION ENHANCED X-RAY IMAGING OF ARTICULAR CARTILAGE

(76) Inventors: Leroy Dean Chapman, 4 Vermont Cir., Bolingbrook, IL (US) 60440-1319; Moumen O. Hasnah, 1400 N. Lake Shore Dr., 21-H, Chicago, IL (US) 60610; Oral Oltulu, 2907 S. Lowe, Apt. 2R, Chicago, IL (US) 60616; Zhong Zhong, 96 University Heights Dr., Stony Brook, NY (US) 11790; Juergen Mollenhauer, Am Ziegelteich 5, D-07607 Eisenberg (DE); Carol Muehleman, 5043 Coyle Ave., Skokie, IL (US) 60077; Klaus Kuettner, 445 W. Briar Pl., Chicago, IL (US) 60657-4710; Matthias Aurich, c/o Eberhard Aurich, Marktsteig 70, D-09212 Limbach-Oberfrohna (DE); Etta D. Pisano, 105 Majestic Ct., Chapel Hill, NC (US) 27514; R. Eugene Johnston, 103 Colburn Point, Chapel Hill, NC (US) 27516; William Craig Thomlinson, Immeuble Vaucanson 10 Allées Résidence St. Mury, 38240 Meylan (FR); Dale Sayers, 1415 Park Dr., Raleigh, NC (US) 27605

( * ) Notice: Subject to any disclaimer, the term of this patent is extended or adjusted under 35 U.S.C. 154(b) by 0 days.

(21) Appl. No.: 09/836,845

(22) Filed: Apr. 17, 2001

(65) Prior Publication Data

US 2002/0027970 A1 Mar. 7, 2002

Related U.S. Application Data

(60) Provisional application No. 60/197,547, filed on Apr. 17, 2000.

(51) Int. Cl.$^7$ .................................................. G01T 1/36
(52) U.S. Cl. ........................................... 378/82; 378/84
(58) Field of Search ............................... 378/82, 84, 85

(56) References Cited

U.S. PATENT DOCUMENTS

| | | | |
|---|---|---|---|
| 4,599,741 | A | 7/1986 | Wittry |
| 5,245,648 | A | 9/1993 | Kinney et al. |
| 5,259,013 | A | 11/1993 | Kuriyama et al. |
| 5,319,694 | A | 6/1994 | Ingal et al. |
| 5,428,657 | A | 6/1995 | Papanicolopoulos et al. |
| 5,579,363 | A | 11/1996 | Ingal et al. |
| 5,805,662 | A | 9/1998 | Kurbatov et al. |
| 5,987,095 | A | 11/1999 | Chapman et al. |
| 6,035,227 | A | 3/2000 | Shmueli |
| 6,038,285 | A | 3/2000 | Zhong et al. |

FOREIGN PATENT DOCUMENTS

WO 95/05725 2/1995

OTHER PUBLICATIONS

D. Chapman, W. Thomlinson, R.E. Johnson, D. Washburn, E. Pisano. N. Gmür, Z. Zhong, R. Menk, F. Arfelli and D. Sayers, *X–Ray Refraction Imaging* (*XRI*) *Applied to Mammography*, published Oct. 31, 1997.

V.N. Ingal and E.A. Beliaevskaya, *Phase Dispersion Introscopy*, (published prior to Oct. 16, 1996).

(List continued on next page.)

*Primary Examiner*—Craig E. Church
(74) *Attorney, Agent, or Firm*—Pauley Petersen Kime & Erickson

(57) ABSTRACT

A method and system for detecting an image of an object, particularly a soft tissue material. A generated x-ray beam is transmitted through the soft tissue material. A transmitted beam is directed at an angle of incidence upon a crystal analyzer. An image of the object is detected from a beam diffracted from the crystal analyzer either at or near a peak of a rocking curve of the crystal analyzer. The method and system of this invention is particularly useful for analyzing images of cartilage.

15 Claims, 15 Drawing Sheets

OTHER PUBLICATIONS

V.N. Ingal and E.A. Beliaevskaya, *X–ray plane–wave topography observation of the phase contrast from a non–crystalline object, J. Phys. D: Appl. Phys.* 28 (1995) 2314–2317.

V.N. Ingal and E.A. Belyaevskaya, *Method of phase–dispersion introscopy, Tech. Phys.* 42 (1), Jan. 1997.

V.N. Ingal and E.A. Beliaevskaya, *Phase dispersion radiography of biological objects, Physica Medica*, vol. X11, No. 2, Apr.–Jun. 1996.

V.A. Bushuev, V.N. Ingal and E.A. Belyaevskaya, *Dynamical Theory of Images Generated by Noncrystalline Objects for the Method of Phase–Dispersive Introscopy, Crystallography Reports*, vol. 41, No. 5, 1996, pp. 766–774.

V.A. bushuev, E.A. Beliaevskaya and V.N. Ingal, *Wave–optical description of X–ray phase contrast images of weakly absorbing non–crystalline objects, II Nuovo Cimento*, vol. 19D, No. 2–4, Feb.–Apr. 1997.

V.N. Ingal and E.A. Beliaevskaya, *Imaging of biological objects in the plane–wave diffraction scheme, II Nuovo Cimento*, vol. 19D, No. 2–4, Feb.–Apr. 1997.

V.N. Ingal and E.A. Beliaevskaya, *Phase Dispersion Introscopy, Surface Investigation.* vol. 12, pp. 441–450, 1997.

Tetsuya Ishikawa, Seishi Kikuta and Kazutaka Kohra, *Angle–Resolved Plane Wave X–Ray Topography, Japanese Journal of Applied Physics*, vol. 24, No. 7, Jul., 1985, pp. L559–L562.

R.C. Blasdell and A.T. Macrander, *Prototype grooved and spherically bent Si backscattering crystal analyzer for meV resolution inelastic x–ray scattering, Review of Scientific Instruments*, vol. 66, No. 2, Feb. 1995, pp. 2075–2077, New York.

Undamaged

Slight Damage

Moderate Damage

Severe Damage

Undamaged

Slight Damage

Moderate Damage

Severe Damage

Undamaged

Slight Damage

Moderate Damage

Severe Damage

DIFFRACTION ENHANCED X-RAY IMAGING OF ARTICULAR CARTILAGE

CROSS REFERENCE TO RELATED APPLICATION

This application claims the benefit of U.S. Provisional Application No. 60/197,547, filed Apr. 17, 2000.

BACKGROUND OF THE INVENTION

1. Field of the Invention

This invention relates to a contrast mechanism referred to as extinction contrast which can be used for a variety of x-ray imaging applications. The method and system of this invention relates to an x-ray imaging modality that uses an analyzer crystal after the object. The imaging contrast of this invention is based on attenuation and refraction.

2. Description of Related Art

One type of diffraction enhanced imaging (DEI) is described in Chapman et al., U.S. Pat. No. 5,987,095.

Articular cartilage covers the ends of bones in synovial joints and provides elasticity, distribution of load, resistance to compressive forces, smooth articulation and cushioning of the subchondral bone during joint movements. Tissue is composed of collagen, primarily type II collagen, entrapping compressed proteoglycan aggregates.

The degeneration of articular cartilage is a component of pathological processes that result in the destruction of the tissue and leads to the deformation of the entire joint. This serious condition, known as osteoarthritis, includes a number of related, overlapping osteoarthritic disorders that are among the leading causes of immobilization within our society and affects probably 85% of elderly people. Use-related joint pain is one of the first signs of disease; however, pain is not always an early warning sign. By the time pain becomes a symptom, successful conservative treatments that could lead to regeneration of the tissue are too late. Presently, several operative methods, including total joint replacement, exist for some but not all the joints. Conventional procedures for repairing of transplanting articular cartilage do not restore a normal articular surface.

Techniques have been applied to access the health or disease of articular cartilage based on x-ray, ultrasound or nuclear magnetic resonance. Among these techniques, conventional radiography has the highest resolution and is the first and most frequently used imaging method to detect joint abnormalities. Conventional radiographs allow the evaluation of articular cartilage only indirectly through the measurement of the height of the joint space, the distance between the corresponding bone surfaces within a joint. Consequently, conventional radiography is sensitive only in cases of advanced disease. Focal cartilage defects or structural abnormalities in early stages of the degenerative process are generally not visible in radiographs.

Conventional x-ray radiography relies on x-ray absorption differences between regions of the object to provide image contrast. Cartilage tissue has little x-ray absorption contrast because the x-ray absorption is similar to soft tissue and synovial fluid. Therefore cartilage cannot be easily seen in conventional radiograph. Diffraction Enhanced Imaging (DEI) is a x-ray radiographic technique that derives contrast from x-ray refraction and scatter rejection (extinction) in addition to the absorption of conventional radiography. These two new contrast sources can in some cases allow visualization of features that are not possible using conventional methods. Certain of DEI are described in U.S. Pat. No. 5,987,095, the entire disclosure of which is incorporated into the specification by reference. The method of this invention uses highly collimated x-rays prepared by x-ray diffraction from perfect single-crystal silicon. These collimated x-rays are of single x-ray energy, practically monochromatic, and are used as the beam to image an object. A schematic of the DEI setup used at the synchrotron is shown in FIG. 1. In this case, the collimated x-rays are prepared by the two crystal sets identified as the Si (3,3,3) monochromator. Once this beam passes through the object, another crystal of the same orientation and using the same reflection is introduced. This crystal is called the analyzer. If this crystal is rotated about an axis perpendicular to the plane shown in FIG. 1, the crystal will rotate through the Bragg condition for diffraction and the diffracted intensity will trace out a profile that is called the rocking curve. The profile will be roughly triangular and will have peak intensity close to that of the beam intensity striking the analyzer crystal. The width of the profile is typically a few microradians wide (3.6 microradians within a full width of half maximum (FWHM) at 18 keV using the Si (3,3,3) reflection). The character of the images obtained change depending on the setting of the analyzer crystal. To extract refraction information, the analyzer is typically set to the half intensity points on the low and high angle sides of the rocking curve. For optimal scatter rejection sensitivity, the analyzer is typically set to the peak of the rocking curve. To image the rejected scatter, the analyzer is set in the wings of the rocking curve.

The DEI method and system of this invention have been applied to image human articular cartilage from the distal part (talas) of the ankle (talocrural) joint that are eight macroscopically normal or display damages typical of early degenerative stages. A human ankle joint indicating the position of the talus within a foot skeleton is shown in FIG. 2.

The tali were obtained within 24 hours of death through the Regional Organ Bank of Illinois with institutional approval. None of the 12 donors used in this study has a known history of osteoarthritic disease. All tali were fixed in 4% paraformaldehyde. For the normal ankles (n=4), the ages were 34 to 54 years, and for the damaged ankles (n=8) that ages were 51 to 66 years. All experiments were performed at the X15A beamline at the National Synchrotron Light Source, Brookhaven National Laboratory, Upton, N.Y. The tali were x-rayed in a posterior to anterior direction.

Examples of a normal and several damaged tali with corresponding DEI according to this invention are shown in FIGS. 3, 4 and 5. The cartilage tissue is clearly detected and distinguished from bone. These images were acquired at an 18 keV x-ray photon energy. The structure of cartilage on the normal talus looks homogeneous, with an average height of 1.5 mm and moderate density ( FIG. 4 and FIG. 6 at 18 keV and FIG. 10 at 30 keV). This pattern changes in damaged cartilage, the tissue is no longer homogeneous but shows patterns that suggest structural alterations (FIGS. 7, 8, 9 at 18 keV and FIGS. 11, 12, 13 at 30 keV) and that correspond with the sites of macroscopic damage (compare with photographs in FIGS. 15, 16, 17).

At higher magnification of certain areas, distinct structural alterations are visible. Of special interest are the thin white lines on a dark background (arrows shown in FIGS. 11–17). It is possible that the white lines represent certain structural changes which give rise to specific refraction patterns, extinction effects and/or absorption contrasts detected by the DEI imaging system according to this invention, which would most likely develop at the edges of cartilage fibrillations, fissures or defects. However, condensed collagen fibrils may also cause such effects. The contrast may further be enhanced because the normally entrapped large proteoglycans are lost due to the damage of the collagen network and therefore the absorption of the x-ray beam is different in this area.

An example of how the character of a subject image changes depending on the setting of the analyzer crystal can be seen in FIG. 18. This is a rocking curve with the corresponding images of the talar dome at various analyzer crystal angles and at the 30 keV energy level. Note the change in appearance of the contrast heterogeneities observed in the images throughout the rocking curve. In the subsequent data sets, images were obtained from at or near the top of the rocking curve (unless specified otherwise) and at either 18 keV or 30 keV, as specified.

As used in the claims and throughout this specification the phrase "at or near the peak of the rocking curve angle" is intended to relate to at 18 keV using the silicon (3, 3, 3) reflection within ± about 1.0 to about 1.8 microradians of the angle of the crystal analyzer. Changing the energy level or changing the reflection will alter the range of microradians of the angle of the crystal analyzer, as would be apparent to a person skilled in the art of diffraction physics of crystals.

The diffraction enhanced (DE) image of a portion of an osteoarthritic knee removed in the course of total knee replacement is shown in FIG. 19. At this stage, only small areas of the joint surface are still covered with an intensely modified cartilage. Specifically, the DE image (FIG. 19) depicts a small 3 cm wide segment of such residual cartilage on top of the femoral bone. Major horizontal heterogeneities in contrast are visible. Further analysis is required to determine the nature of these contrasts as condensed/collapsed collagen fiber networks or perhaps a reflection of another unknown molecular feature within the tissue. The regular radiographic image of the same area does not show the cartilage or these features (FIG. 20).

Preliminarily, the contrast heterogeneity features observed below the cartilage surface in the DE images in some of the specimens have been histologically validated. FIG. 21 shows a section of talar dome as it is grossly observed (FIG. 21) and in its DE image at 18 keV (FIG. 22) and at 30 keV (FIG. 23). A normal-looking region of the specimen as depicted in square number 1 can be seen in its Safranin O/fast green histological preparation in FIG. 24. Under polarized light, the same specimen displays a normal pattern of birefringence in the superficial and deep zones (FIG. 25). A region of the talar dome displaying a "bubbled" region of cartilage ("chondrophyte") in which contrast heterogeneities (dark spots) can be seen is depicted in square number 2. FIG. 26 is the Safranin O/fast green histological preparation of the chondrophyte region. The dark spot observed in the DE image in square number 2 appears, histologically, to be a vacuolated space (e.g. blister) in the cartilage surrounded by cartilage in a state of degeneration/remodeling. The polarized microscopic section of the same region (FIG. 27) shows that the collagen fibers surrounding the "vacuolation" have lost their normal birefringent pattern and thus display disorganization. It is apparent that the DE images reflect the general status of cartilage normality or degeneration in these specimens.

Although DEI is in its infancy in terms of development, an assessment of the potential of DEI for practical applicability in intact joints is warranted at this time. The DE images of the intact knee joint with all of its surrounding soft tissues, except skin, can be seen in FIGS. 28 and 29. FIG. 28 was taken at or near the top of the rocking curve and FIG. 29 was taken at −3.6 microradians. These are an image of the medial femoral and tibial condyles with their associated articular hyaline cartilage and fibrocartilaginous menisci. The arrows point to the boundaries of the articular hyaline cartilage surfaces. Both the articular cartilage and menisci can be delineated even through the surrounding tissues.

It is possible to image animal articular cartilage with DEI. FIG. 30 shows cartilage and bone of the femoral condyle of a New Zealand white rabbit. FIG. 31 is a DE image of the intact knee joint showing joint tissues including the articular cartilage of the femoral condyles. This is quite remarkable considering that the cartilage is only approximately 110$\mu$ thick. It is also noteworthy that the articular cartilage can be seen even through the surrounding soft tissues, including skin and hair. FIG. 32 shows the DE image of a disarticulated femur taken from a rabbit knee joint that had been injected with the cartilage matrix damaging enzyme, chymopapain, three weeks prior to the animal sacrifice. Small areas of, what appears to be, damage (in the form of refraction/extinction features) correspond to damage on the right femoral condyle as depicted histologically (see the arrow in FIG. 32).

Application of the DEI method and system of this invention, particularly as it applies shows improved contrast of specific structures within the human breast tissue in a clinical setup. The DEI method and system of this invention can extend skeletal radiology, in addition to its use for imaging of cartilage. X-rays are ideal to evaluate changes in the subchondral bone which are a major component of osteoarthritic disorders.

SUMMARY OF THE INVENTION

Standard radiographic evaluation of osteoarthritic disorders involves detecting the narrowing that occurs in a joint space as a joint cartilage is destroyed during a disease process only because that cartilage tissue is invisible in x-ray imaging. A high resolution image of human articular cartilage from the talar dome of an ankle joint, for example, can now be obtained using Diffraction Enhanced Imaging (DEI), an x-ray radiographic technique that has contrast from x-ray refraction, scatter rejection and absorption. Defects, structural abnormalities, and loss of articular cartilage can be detected in the tissue using the DEI method and system according to this invention. DEI can provide information about an internal structure of cartilage before other visual evidence of disease has evolved.

The DEI method and system of this invention can be used to explore the application of high intensity and inherent vertical collimation of synchrotron radiation to the creation of a monoenergetic line scan system for radiography of thick absorbing objects. A x-ray analyzer crystal can be used as a scatter rejection optic to diffract a beam that is transmitted through an imaged object. With this scatter rejection optic the system of this invention may be sensitive to refractive index effects within the imaged object and the x-ray absorption and scattering by the object. The setting of the analyzer at or near the top of the rocking curve, places the analyzer at a setting that rejects those rays that are scattered or refracted. The result is to develop image contrast from the structures that create this effect. Cartilage is a tissue of this type of structure.

Images taken with an analyzer and normal radiographs of objects show that the rejection of scatter can be a major source of contrast with the DEI imaging geometry. With the DEI imaging method and system of this invention, additional contrast can be many times the normal absorption contrast of an object. To account for additional source of image contrast in DEI images, the term apparent absorption is used and relates to the combined absorption and extinction processes. Extinction relates to the loss of intensity due to scattering that occurs as the beam traverses the object and this type of extinction is commonly identified as secondary extinction. Use of the term extinction in this invention is slightly different from use in optics where the term extinction includes absorption and scattering power loss. The power loss from the direct beam due to scattering is referred to as extinction.

Sources of the enhanced image contrast explain why increased contrast is a result of extinction effects, which provides opportunity for imaging based on these properties. Because the contrast of an image based on extinction can be much higher than contrast based on x-ray attenuation, it is possible to detect smaller inhomogeneities, such as tumors in medical images or micro-fractures in industrial parts.

Monochromator and analyzer system capabilities to resolve refraction effects depend on the imaging energy as 1/energy. The scattering properties of various elements are energy dependent as $1/\text{energy}^2$ which will allow optimization of imaging system energy to maximize contrast due to extinction while maintaining refraction contrast. Thus, the modality may be optimally applied at higher x-ray energies, which provides better penetration in non-destructive testing and/or lower doses in medical imaging.

It is known to apply diffractive optics to imaging problems for observing refraction and ultra-small angle scattering contrast effects. The results quantify the role of ultra-small angle scattering and the scatter rejection in the DEI method and system of this invention. Also, imaging experiments based on imaging the scatter from objects, for example scatter imaging references, are known. This known technique relies on imaging a direct beam that is mostly devoid of scatter and is complementary to scatter imaging. There is an interest in phase contrast imaging that uses high transverse coherence of small source points, such as that of third-generation synchrotron sources. Phase contrast images are limited to either thin objects or high x-ray imaging energies. The DEI method and system of this invention is similar to phase contrast imaging due to sensitivity to refraction. However, the additional benefit of the analyzer crystal in this invention allows refraction determination in highly absorbing objects and produces additional contrast due to its scatter rejection capabilities.

With the DEI imaging according to this invention, it is possible to visualize articular cartilage using the new x-ray modality, referred to as DEI. Moreover, the combination of the high spatial resolution that can be achieved with x-rays, and the independent detection of refraction patterns, scatter rejection and x-ray absorption make the method of the invention capable of detecting not only articular cartilage and gross cartilage defects but also structural abnormalities within the tissue. With the DEI imaging of this invention, it is possible to detect cartilage degeneration even in early stages, such as before any clinical evidence of disease evolves. The DEI imaging of this invention can be used as a part of a new x-ray generation in research as well as in clinical radiology, especially in skeletal x-ray, and in other areas where soft tissue contrast needs to be enhanced.

BRIEF DESCRIPTION OF THE DRAWINGS

FIGS. 21–27 show cartilage of a talus demonstrating a degenerative site, wherein:

FIG. 21 shows a photograph of the margin of a talar dome and the arrow points to a lesion or “chondrophyte”;

FIG. 22 is a DE image of the lesion site at 18 keV;

FIG. 23 is a DE image of the lesion site at 30 keV, wherein the arrows in both FIGS. 22 and 23 point to the cartilage/bone interface which appears to be interrupted at the far right in the 30 keV image shown in FIG. 23;

FIG. 24 is an image of a Safranin O stained section taken from a normal looking region;

FIG. 25 is an image of a Picrosirius red stained histological section under polarizing light showing the normal birefringent pattern in the superficial and deep zones (*);

FIG. 26 is an image of a Safranin O staining of a histological section taken from square number 2, which is of interest because the lessened degree of contrast observed at the right corner of the image taken at 18 keV (in FIG. 22) corresponds to regions of proteoglycan depletion seen histologically; and FIG. 27 is an image of a Picrosirius red stained section under polarizing light of the area in square number 2, wherein the apparent space in the center and the lack of normal birefringence in the surrounding area indicate a disorientation of collagen fibers (all histological sections are magnified 2×).

FIGS. 28 and 29 show DE images of the medial condyle of an intact knee joint, the images taken with all surrounding soft tissue, except the skin, in place, and the articular hyaline cartilage (at arrows) and fibroelastic menisci are visible even through the surrounding connective tissues, wherein:

FIG. 28 is a DE image taken at the top of the rocking curve; and

FIG. 29 is a DE image taken at −3.6 microradians from the top of the rocking curve.

FIGS. 33–35 each is an image taken at 18 keV of the American College of Radiology mammography test object showing the tumor simulations with 1.00 mm, 0.75 mm, 0.59 mm and 0.25 mm thickness, wherein:

FIG. 33 is a DE image taken at the top of the rocking curve;

FIG. 34 is a conventional radiograph of the simulated tumors; and

FIG. 35 is a DE image taken at −3.6 microradians from the top of the rocking curve.

FIGS. 36 and 37 show an example extinction from ACR tumor simulations at 18 keV, wherein:

FIG. 36 is a DE image at top of rocking curve showing location where fixed x-ray beam strikes the tumor simulations (similar to FIG. 33); and FIG. 37 is a rocking curve showing position along ACR where tumor simulations are located, the angular axis for the rocking curve and intensity, showing regions where the tumor simulations are located at the top of the rocking curve at which the intensity is depressed and showing the intensity in the wings (away from the peak) at which the intensity is increased.

DESCRIPTION OF PREFERRED EMBODIMENTS

Figure 1:
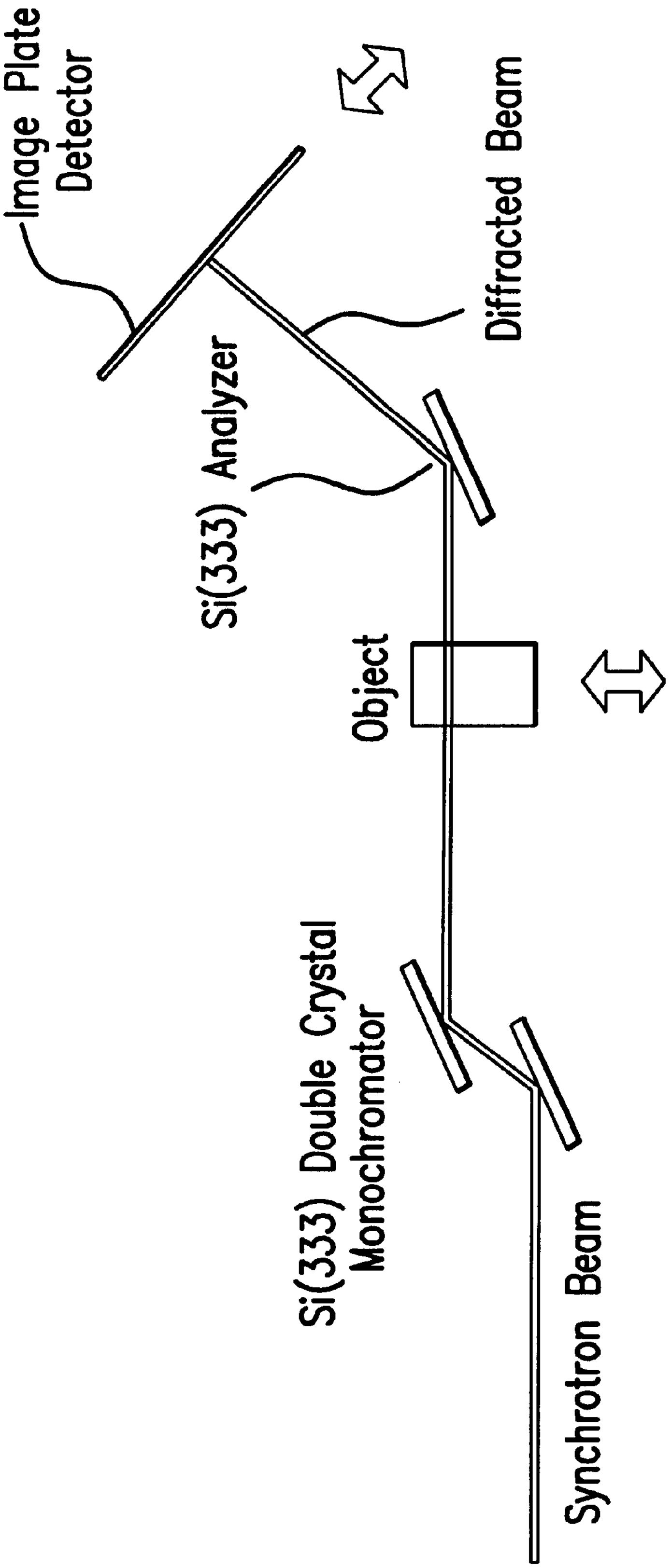
FIG. 1 is a schematic representation of a DEI system, according to one preferred embodiment of this invention, wherein the synchrotron beam is incident from the left and the energy is selected by the Si (3,3,3) monochromator. This beam is passed through the object and is analyzed by a matching Si (3,3,3) crystal after the object. The diffracted beam is detected as an image on a stimulable phosphor plate (image plate). The beam from the synchrotron is a fan beam that extends into and out of the plane of the paper. To create the planar image of the object, the object and the detector are scanned perpendicular to the beams as shown with the arrows.
Figure 2:
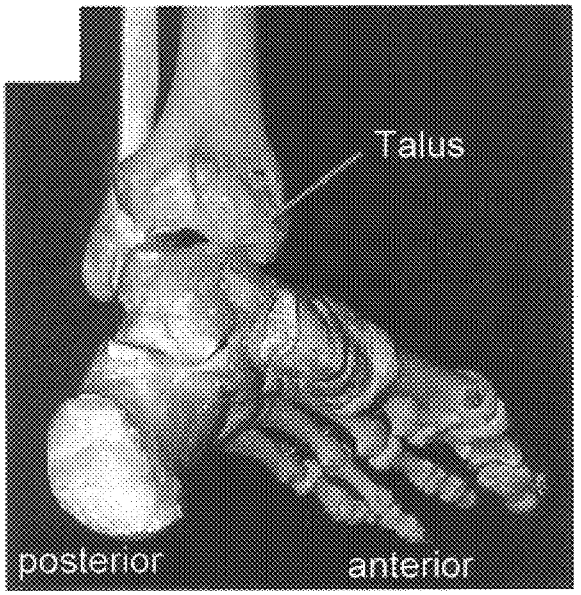
FIG. 2 is an image of a medial aspect of the ankle joint from a left foot of a human skeleton. This joint is formed by the tibia and fibula articulating with the talus (see arrow) to form the talocrural (ankle) joint.
Figure 3:
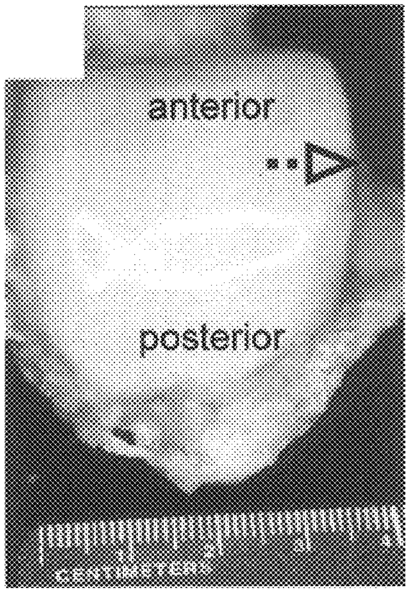
FIG. 3 is a photograph that shows an image of a superior surface of the talus. The arrow indicates the orientation of the talus in relation to FIGS. 4 and 5.
Figure 4:
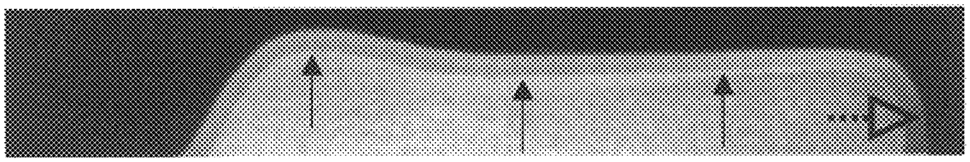
FIG. 4 is a DEI image at 30 keV, acquired according to the method and system of this invention, with the x-ray beam parallel to the articular surface from posterior to anterior. The fine arrows indicate the bone/cartilage interface, with the cartilage (approx. 1.5 mm in height) as the less bright layer. The large arrow indicates the orientation of the DEI image relative to the macroscopic image in FIG. 3. The actual resolution of the DEI image is approximately 100 $\mu$m, the image is approximately three-fold magnified as compared to the proportions of the talus.
Figure 5:
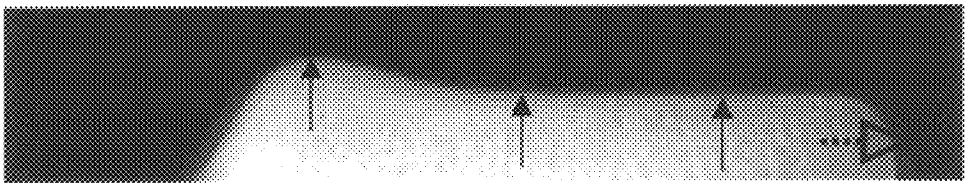
FIG. 5 is a radiograph of the talus shown in FIGS. 3 and 4.
Figure 6:
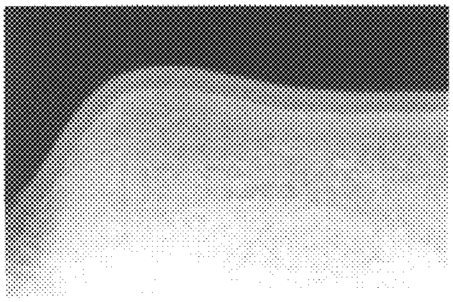
FIGS. 6–17 each shows a section of DEI from the talar dome of the ankle joint. DEI of normal and damaged articular cartilage from the talus of a human ankle is shown at 30 keV (top row) and 18 keV (middle row) with the corresponding macroscopic pictures (bottom row). The DEI cartilage tissue image of the intact talus (FIG. 6 and FIG. 10) shows a homogenous and moderately dense structure. In the damaged tali (FIGS. 7, 8 and 9, and FIGS. 11, 12 and 13) the degenerative sites (arrows) are clearly detected by distinctive structural inhomogeneities within the cartilage. In order to better visualize the damage in the photographs (FIGS. 14, 15, 16 and 17), the samples have been slightly rotated compared to the positioning for the DEI. The arrows indicate particular sites of lesions.
Figure 7:
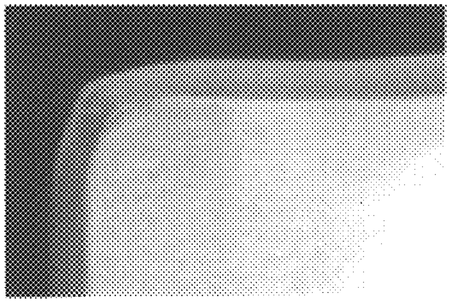
Figure 8:
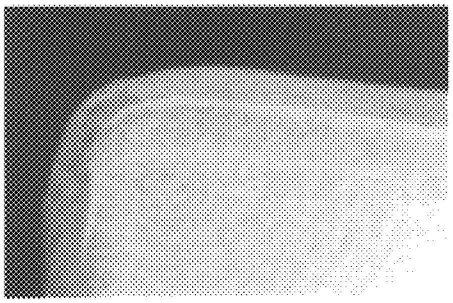
Figure 9:
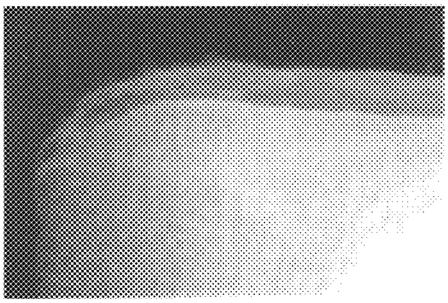
Figure 10:
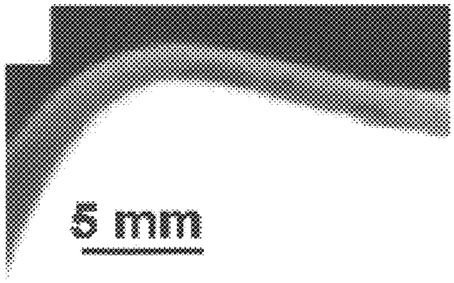
Figure 11:
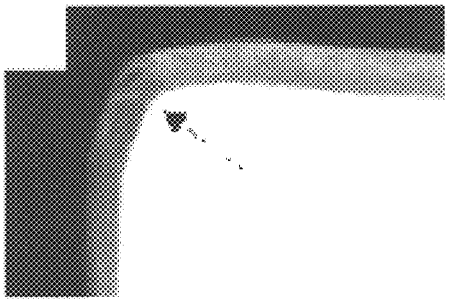
Figure 12:
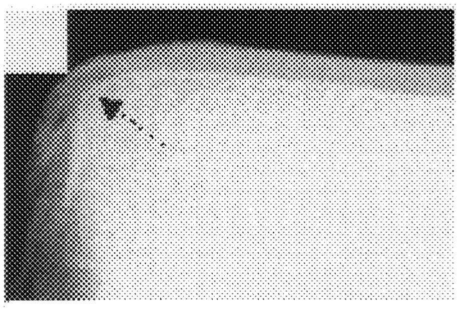
Figure 13:
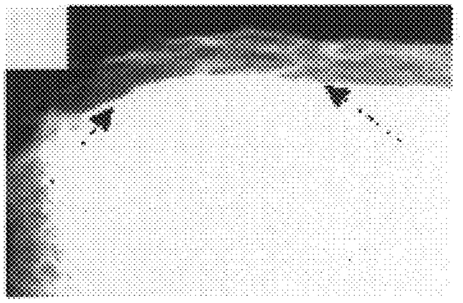
Figure 14:
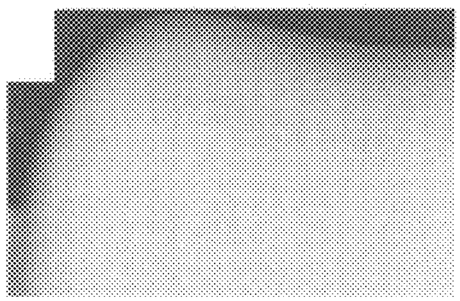
Figure 15:
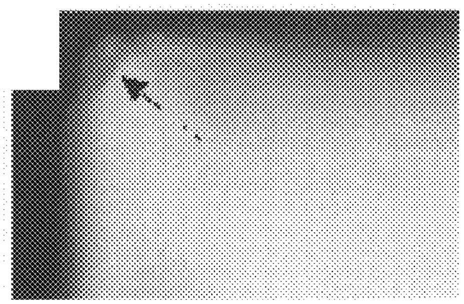
Figure 16:
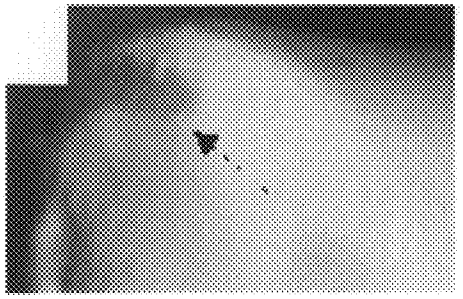
Figure 17:
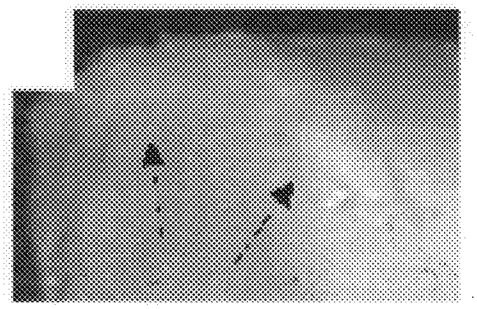
Figure 18:
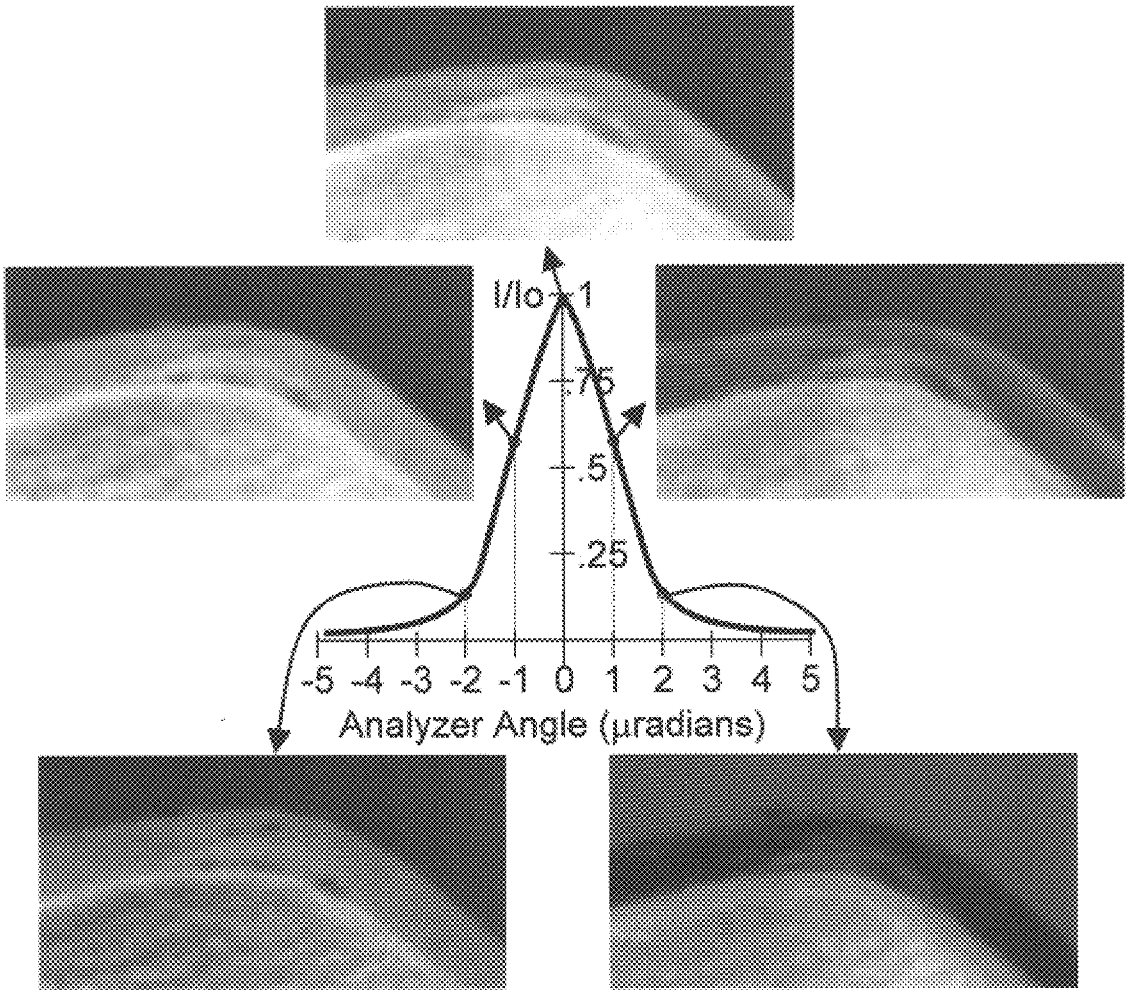
FIG. 18 shows DEI images of articular cartilage taken along different points of the rocking curve. An illustration showing the alterations in structural information from articular cartilage as the analyzer setting is taken through the rocking curve at 30 keV. The locations or points at which the images are taken are indicated on the rocking curve. Appearance of inhomogeneities within the cartilage tissue change at various points in the rocking curve.
Figure 19:
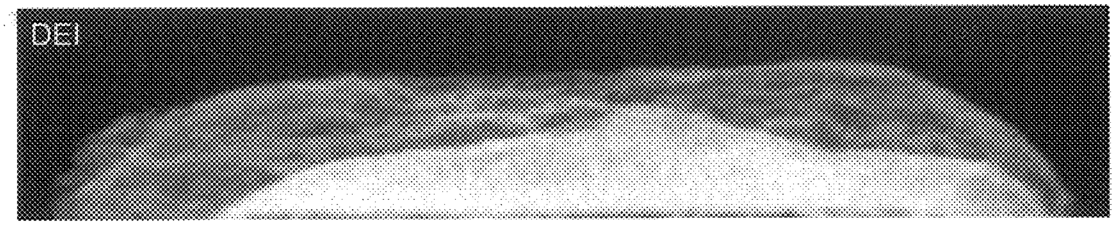
FIG. 19 shows a DE image of a part of an osteoarthritic knee. A resected segment from a femural condyle of a 67-year old patient who underwent total knee joint replacement due to endstage osteoarthritis is shown by 18 keV-DEI. In DEI, the residual cartilage is clearly visible and displays major structural reorganization of the extracellular matrix, as compared to the healthy cartilage shown in FIGS. 4, 5, 6 and 10.
Figure 20:
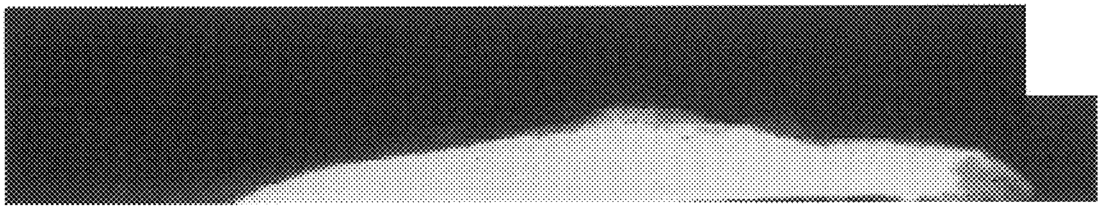
FIG. 20 shows a conventional radiograph from the same area shown in FIG. 19 which does not show the structural features within the cartilage tissue.
Figure 21:
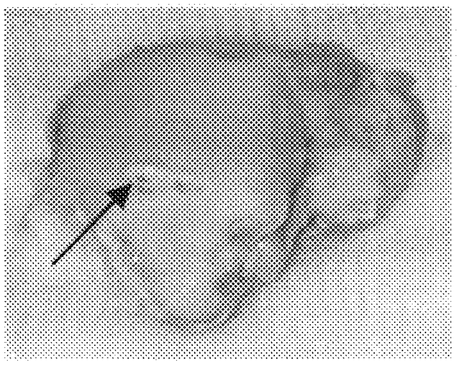
Figure 22:
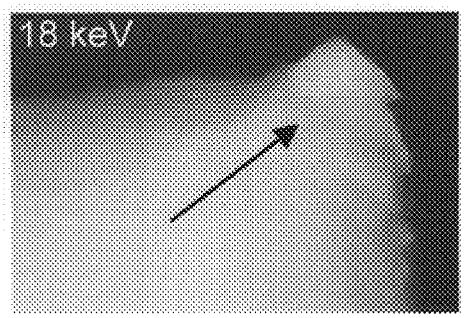
Figure 23:
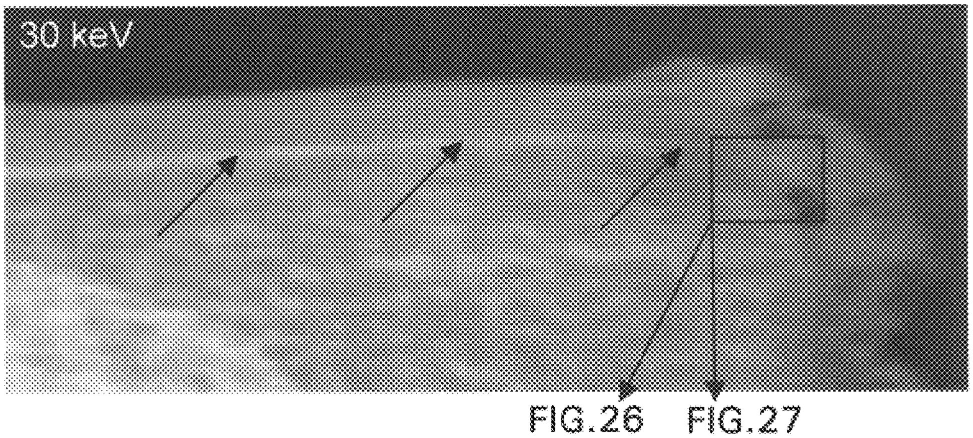
Figure 24:
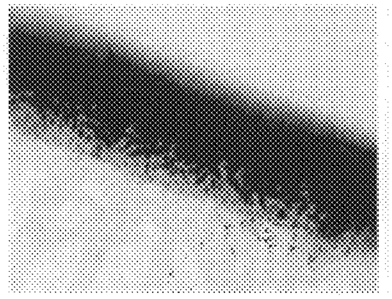
Figure 25:
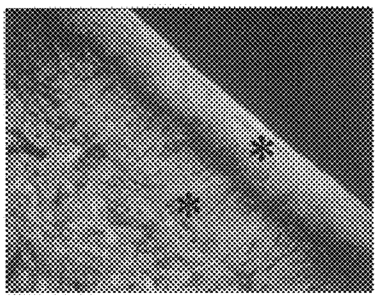
Figure 26:
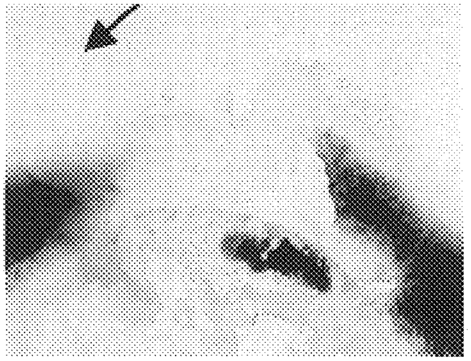
Figure 27:
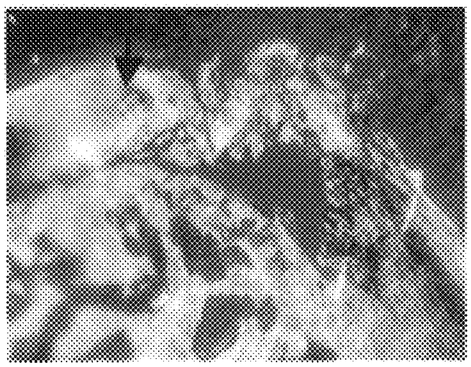
Figure 28:
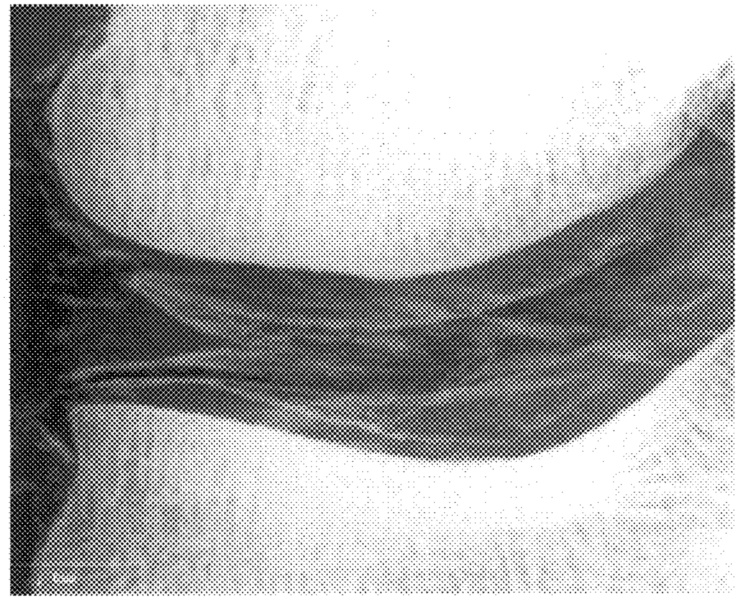
Figure 29:
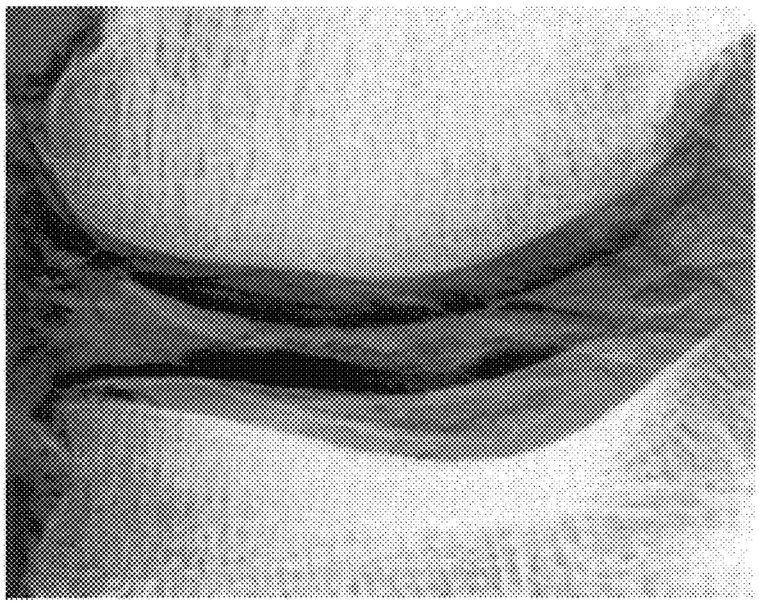
Figure 30:
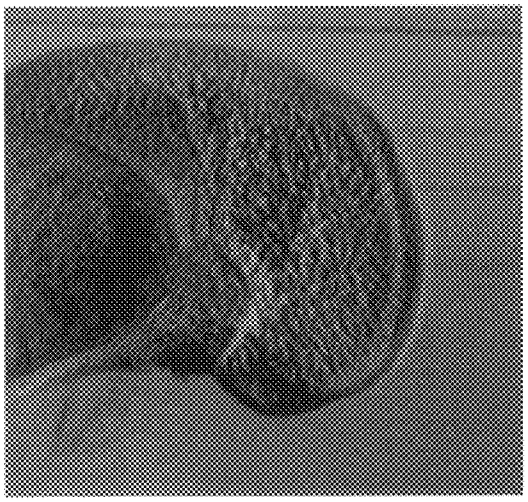
FIG. 30 is a DE image of a disarticulated joint of a New Zealand white rabbit taken at 18 keV.
Figure 31:
FIG. 31 is a DE image of an intact joint of a New Zealand white rabbit taken at 18 keV.
Figure 32:
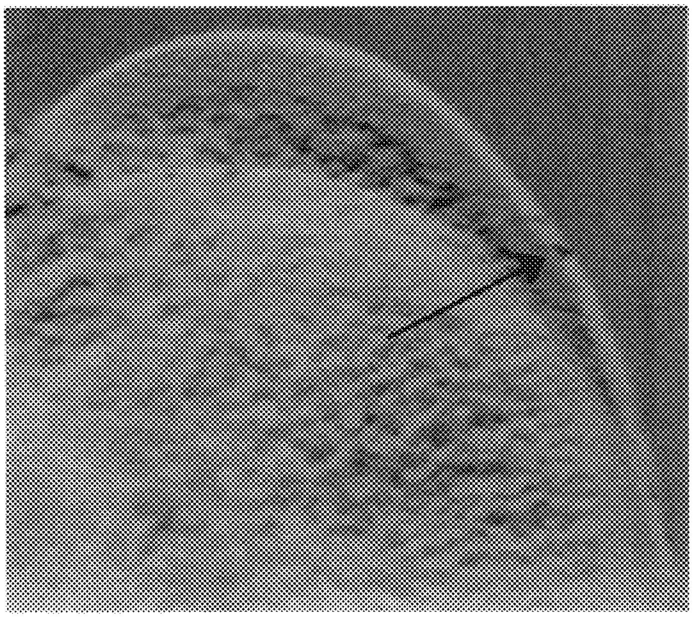
FIG. 32 is a DE image at 18 keV of a disarticulated femur taken from a rabbit knee joint that had been injected with the cartilage matrix damaging enzyme, chymopapain, three weeks prior to the animal sacrifice, showing small areas of, what appears to be, damage as indicated by the arrow.

In radiography, intensity transmitted through an object is an important factor. An analyzer crystal in an imaging system will reject scatter produced in the object and will introduce sensitivity to refraction. These effects can be quantified and compared with the results using direct measurements with an analyzer and with normal radiographs of objects. For this analysis, an incoherently scattered (Compton) and wide-angle coherent scattering ($\sin\theta/\lambda > 10^{-2}$ $nm^{-1}$) is ignored. In addition, complications associated with refraction are ignored to emphasize the extinction aspects. Thus, equations developed according to this invention apply to systems with normal absorption, refraction and ultra-small angle scattering.

As a beam prepared by a perfect crystal monochromator traverses a uniform object with absorption and ultra-small angle scattering and is subsequently analyzed by a perfect crystal, a photon count rate (photons/sec) observed in a detector pixel, $n_{DEI}(\theta_A)$, can be represented by the equation:

$$n_{DEI}(\theta_A)=n_D(\theta_A)+n_S(\theta_A) \qquad \text{Equation 1}$$

where $n_D(\theta_A)$ represents a photon count rate detected from a direct or unscattered beam and $n_S(\theta_A)$ represents a detected photon count rate from scatter arriving into a same pixel. A direct component can be found by assuming that the beam striking the object suffers intensity losses from absorption and scattering according to the equation:

$$dn_D=(-I_0\Delta A\ \mu/\rho T\ \rho dt-I_0\Delta A\sigma_S\rho_S dt)R(\theta_A) \qquad \text{Equation 2}$$

where $I_0$ is an intensity (photons/area/sec) striking the dt thickness increment of material that will arrive at a pixel in the detector of area ΔA, $dn_D$ is a change in x-ray count rate that will strike the detector pixel in traversing the dt thickness increment, $\mu/\rho T$ is the total mass absorption coefficient which includes coherent and incoherent scattering (isolated atom values), ρ is the mass density, $\sigma_S$ is the total cross-section for scattering due to the presence of organized structures, and $\rho_S$ is a density of scatters per unit volume. $R(\theta_A)$ represents a rocking curve of the analyzer crystal in the beam prepared by a monochromator with $\theta_A$ indicating a setting of the analyzer crystal relative to a peak position when fully tuned with the monochromator. Equation 2 when integrated in thickness through the object, $t_0$, leads to the equation:

$$n_D(\theta_A)=i_0\Delta A e^{-\chi_s t_0} e^{-\mu_T t_0} R(\theta_A) \qquad \text{Equation 3}$$

where $\chi_x=\sigma_S\rho_S$ which is referred to as an extinction coefficient and $\mu_T=\mu/\rho T\ \rho$ is a total attenuation coefficient. Equation 3 applies only for a part of the beam that traverses the object without being scattered and assumes that none of the scatter created by the beam traversing the object is present in the detected beam. In reality, no detector can reject the entire scatter component and will accept some portion of the scatter. The incremental scattered beam intercepted by the detector pixel is represented by the equation:

$$dn_S = I_0 \Delta A e^{-(\mu_T - \chi_S)t}\left(\rho_S \int_{pixel}\int \frac{d\sigma_S}{d\Omega} R(\theta_A) d\Omega\right) e^{-\mu_T(t_0 - t)} dt \quad \text{Equation 4}$$

where $d\sigma_S/d\Omega$ a differential scattering coefficient for x-rays in a near forward direction. The solid angle integral over this scatter distribution is taken over a solid angle of a detector pixel as seen from a scatterer. $I_0(t)$ from Equation 2 describes the incident intensity arriving at the scattering region at depth t, and $e^{-\mu_T(t_0-t)}$ is an attenuation of scatter in a remainder of its path before emerging from the object and striking the detector. The quantity $$\rho_S \int_{pixel}\int \frac{d\sigma_S}{d\Omega} R(\theta_A) d\Omega$$

describes an amount of scatter accepted by the detector pixel as altered by a presence and setting of the analyzer crystal and is referred to as $\chi'_S(\theta_A)$. Integrated through the object thickness, assuming the scattered beams travel the same path as the direct beam leads to the equation:

$$n_S(t_0) = I_0(0)\Delta A \frac{\chi'_S(\theta_A)}{\chi_S}[1 - e^{-\chi_S t_0}] e^{-\mu_T t_0} \quad \text{Equation 5}$$

Equation 5 represents the scatter accepted by the detector in addition to the direct transmitted beam from Equation 2. The amount accepted relates to the ratio $$\frac{\chi'_S(\theta_A)}{\chi_S}$$

which is determined by the detector and scatter rejection geometry imposed by the analyzer. The total count rate seen by the detector is governed by the equation:

$$n_{DEI}(t_0) = I_0(0)\Delta A\left\{e^{-\chi_S t_0} R(\theta_A) + \frac{\chi'_S(\theta_A)}{\chi_S}[1 - e^{-\chi_S t_0}]\right\} e^{-\mu_T t_0} \quad \text{Equation 6}$$

If the scattering distribution is small in relation to acceptance of the detector, then the ratio $$\frac{\chi'_S(\theta_A)}{\chi_S}$$

approaches the value of the rocking curve at the analyzer setting $\theta_A$ or $R(\theta_A)$ and the measured intensity will be the same as for normal absorption.

For the method and system of this invention, a Gaussian scatter distribution can be used. For small angle scattering, the scattered intensity distribution can be described by a Guinier equation. This form will be assumed to arrive at a simple closed solution, although it may not accurately describe an ultra-small scattering from the object. Expressed as a cross-section or probability of scattering x-rays at a deviation angle, $\phi$, from the direct beam is the equation:

$$\rho_S \frac{d\sigma_S}{d\Omega} = \frac{1}{\pi\omega_S^2}\chi_S e^{\frac{\phi^2}{\omega_S^2}} \quad \text{Equation 7}$$

where $\omega_S$ is an angular width of the distribution related to a radius of gyration of the particle size distribution. When integrated over all scattering angles $\phi$, the result is the total extinction coefficient $\chi_S$. With the analyzer crystal in place the amount of scatter that can reach the detector is severely limited by acceptance of the analyzer crystal in the diffraction plane of the analyzer. The acceptance in the plane perpendicular to the diffraction plane is not significantly restricted in the diffraction from the analyzer. Only a single scatter direction is considered because with DEI the scatter is accepted in a direction parallel to the analyzer planes and rejected in a relative perpendicular direction. The scatter accepted by the detector is the integral of this function over the acceptance angle of the detector, which in this case is the reflectivity width of the analyzer crystal, $\omega_D$.

Integrating this relation in Equation 4, produces the equation:

$$\frac{\chi'_S(\theta_A)}{\chi_S} \cong \frac{\omega_D}{\sqrt{\pi}\,\varpi_S} e^{-\frac{\theta_A^2}{\omega_S^2}} \quad \text{Equation 8}$$

where it is assumed that a width of the scattering distribution is larger than a rocking curve width, i.e. $\omega_S >> \omega_D$, and thus the equation:

$$I_{DEI}(\theta_A) = I_D + I_S = i_0 \Delta A e^{-\mu_T t_0} \left\{ e^{-\chi_S t_0} R(\theta_A) + \frac{1}{\sqrt{\pi}} \frac{\omega_D}{\omega_S}[1 - e^{-\chi_S t_0}] e^{-\frac{\theta_A^2}{\omega_S^2}} \right\} \quad \text{Equation 9}$$

where $R(\theta_A)$ is the convoluted reflectivity of the monochromator with the analyzer crystal. In one preferred embodiment of this invention, the monochromator and the analyzer system are in a parallel crystal geometry to avoid dispersion widening of the rocking curve. This equation has two parts. The first part has a width of the rocking curve of the monochromator and the analyzer system, remnants of the original direct beam. The second part has a width determined by an ultra-small angle scattering distribution convoluted with the monochromator and the analyzer system. As the size of the extinction coefficient and thickness of the ultra-small angle scatterer is increased, the direct beam is converted into ultra-small angle scattering. In the case of $\chi_S t >> 1$ this conversion is nearly complete and the direct beam appears lost and only ultra-small angle scattering will remain.

One property of interest is to sum an intensity passed by the analyzer as the analyzer is rocked through the above distribution, integrated intensity. Integrating Equation 8 over $\Delta\theta_A$ leads to the integrated reflecting power and the equation:

$$R = \lfloor e^{-\chi_S t_0}\omega_D + (1 - e^{-\chi_S t_0})\omega_D \rfloor e^{-\mu_T t_0} = e^{-\mu_T t_0}\omega_D \quad \text{Equation 10}$$

In the absence of the object, an integrated reflecting power is $\omega_D$. Equation 10 shows that the scattered intensity arising from the object is not lost but just scattered away in angle and recovered by integrating over the entire profile. In one embodiment of this invention, if the distribution of the scattering is small in comparison to the angular acceptance of the detector pixel, then there is only normal absorption. When the ultra-small angle scattering is rejected, for example when the analyzer crystal is added, then an additional contrast is obtained.

The image contrast arises from comparisons of intensities between two regions of an image. Equation 9 is used to interpret contrast arising from a scattering and absorbing object.

EXAMPLE

Experiments using the method and the system of this invention were performed at the National Synchrotron Light Source 15A Imaging PRT Beamline, at Brookhaven National Laboratory, Upton, N.Y. Preliminary results have rendered an interpretation of refraction and a qualitative description of extinction. One experimental setup is shown in FIG. 1. A white synchrotron beam was made nearly monochromatic by a silicon double-crystal monochromator. One usable energy range of this system, as used, was 15 keV −40 keV. For the measurements described here the beam energy was 18 keV with a bandwidth of 1.5 eV, but could also be 16 keV to 100 keV with a bandwidth of 1.5 eV and 2.6 eV, respectively. An in-hutch monochromator was used to monochromate the beam to provide the imaging beam. The monochromator had silicon (3,3,3)-lattice planes. The type of lattice planes can be selected to determine the refraction and scatter rejection sensitivity. All of the crystals in the system were in the parallel geometry to avoid dispersive effects and to optimize refraction and scatter rejection sensitivity. The imaging beam was approximately 85 mm wide and 1 mm high. The beam entering the experimental enclosure passed through a gas ionization chamber. A rotary shutter was used to control the exposure and limit unnecessary scatter at the detector position. A second ion chamber was used to measure the radiation dose at the surface of an object. Images taken with and without the analyzer were at dose levels comparable to conventional mammography x-ray systems. The object to be imaged was mounted on a scanning stage that was driven by a stepping motor. The x-ray beam transmitted through the object could be imaged either directly as in normal radiography or following diffraction in the vertical plane by a silicon Bragg analyzer.

The detector used in the experiment was a photostimulable phosphor image plate, typically used for radiology, for example a high resolution HR5 and standard resolution ST5 image plates, such as available through Fuji Medical Systems. The image recorded on the plate was digitized, stored and displayed by a Fuji BAS2000 reader and workstation. The spatial resolution of the images was $0.1\times0.1$ mm$^2$. The diffraction angle of the analyzer crystal was finely tuned using a stepper-motor driven translation stage pushing on a long bar attached to an axle to which the crystal was attached, a tangent arm. The resolution limit of the tangent arm was 0.1 microradian and was sufficient for placing the Bragg analyzer crystal at a selected position on its rocking curve.

Because the initial interest was in studying the use of synchrotron imaging for early detection of breast cancers, a mammography phantom was used as the test object to be radiographed. The standard phantom used for quality control in mammography is the American College of Radiology (ACR) phantom manufactured by Gammex RMI: Model 156. The standard phantom contains features that simulate lesions commonly found in breast tissue, namely tumor-like masses (lens-shaped objects of different thicknesses and diameters), simulated micro-calcifications arranged as vertices of five-point stars and cylindrical nylon fibrils. Initially, the simulated tumor masses exhibited a much higher contrast (about 27 times) compared to conventional radiographs. The features are fixed in a wax block contained in a thick acrylic base. The standard phantom approximates a 40 to 45 mm thick compressed breast. Since the x-ray beam was a fan in the horizontal plane (x-y plane), the object and the image plate were simultaneously translated in the vertical direction (z-direction). Scanning was accomplished by a computer controlled stepper motor translation stage that held both the phantom support and a mount for the image plate cassette.

To establish that ultra-small angle scattering had occurred, rocking curves of line regions of the ACR phantom were obtained. In this measurement, the object was positioned in the beam and remained fixed in relation to the beam while the analyzer crystal was rocked in angle. During a scan of the analyzer angle, the image plate detector was scanned in unison to obtain an image of the rocking curve of the object.

Analysis of Experiment

Figure 33:
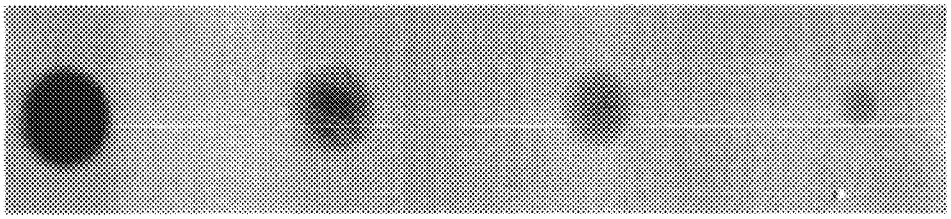
Figure 34:
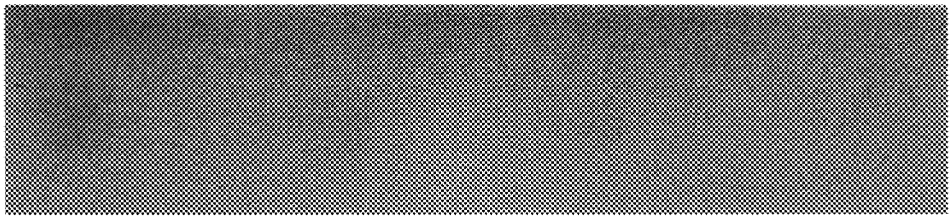
Figure 35:
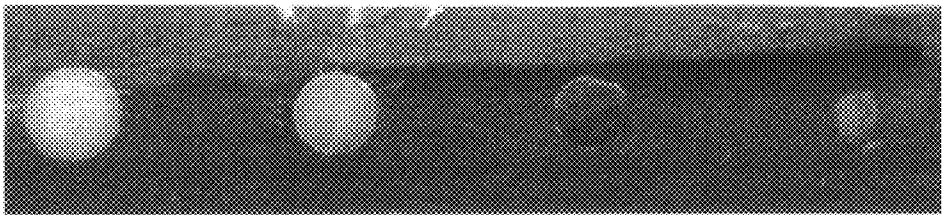

Contrast is defined as a fractional change in intensity, $\Delta I/I$, observed by comparing one region of an image to an adjacent region for background value. Extinction played a major role in the contrast of DEI images obtained according to the method and the system of this invention because of a direct comparison of the non-analyzer or normal radiographs with the images acquired with the analyzer. A comparison of images taken with and without the analyzer is shown in FIGS. 33–35. This is a region of an image of the ACR phantom that centers along the line of tumor simulations. These are spherical caps of Bakelite [Gammex RMI reference] of 1.00, 0.75, 0.50, and 0.25 mm thickness. FIG. 34 is acquired with the analyzer crystal removed and is the normal radiograph of these objects. FIGS. 33 and 35 are acquired with the analyzer. This image is taken with the analyzer at the peak of reflectivity. The measured contrast was found to be −1.5% for the normal radiograph of the thickest 1.00 mm tumor simulation shown in the drawings. The same simulation with the analyzer gives a −40% contrast.

Figure 36:
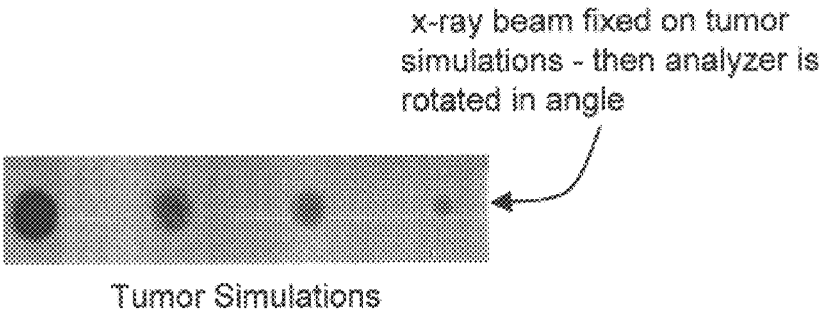
Figure 37:
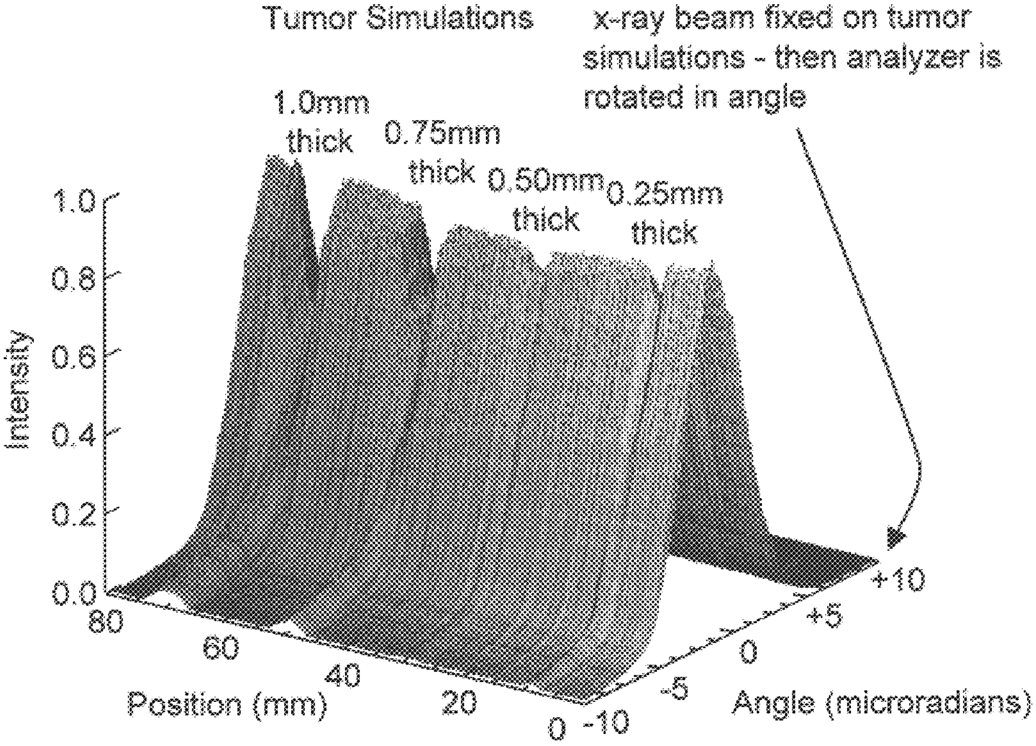

As the analyzer rocking angle is altered from the peak position the contrast is reduced and will pass through zero and the contrast will reverse, resulting from the scatter in the rocking curve wings of the tumor simulation exceeding the background value. This is illustrated in FIG. 35 which shows an image obtained at 72 microradians of the same region of the ACR as shown in FIGS. 33 and 34. The detailed dependence of the intensity obtained as the analyzer angle is varied is shown in FIGS. 36 and 37. The beam is located at a fixed location across the ACR tumor simulations as indicated in FIG. 36. FIG. 37 shows the intensity recorded as the analyzer is rotated in angle about the rocking curve peak. The analyzer was rocked in angle about the peak position and the intensity recorded at each setting on an image plate. The locations of each of the four tumor simulations were marked for reference. At or near the analyzer peak there was a decrease in intensity relative to the background (negative contrast). As the analyzer was rocked away in angle the intensity approached the surrounding value (contrast approximately zero) in the range of ±2 microradians offset. As the offset angle was further increased the contrast reversed due to the scattered x-rays contributing more intensity in the tumor simulation locations compared to the background (positive contrast). This indicated that the objects create ultra-small angle scatter and explains why the normal radiograph of these objects shows little contrast. The angular range falls to background values in approximately a ±15 microradians. This range of deviation angles is too small to be rejected by normal anti-scatter techniques such as anti-scatter grids that can typically reject down to 0.1 degree (2 milliradians).

The ACR phantom represents a case of relatively weak extinction in which some of the direct beam is retained. As the amount of extinction is increased, the amount of surviving direct beam is reduced and eventually is reduced below the level of scattering.

Figure 38:
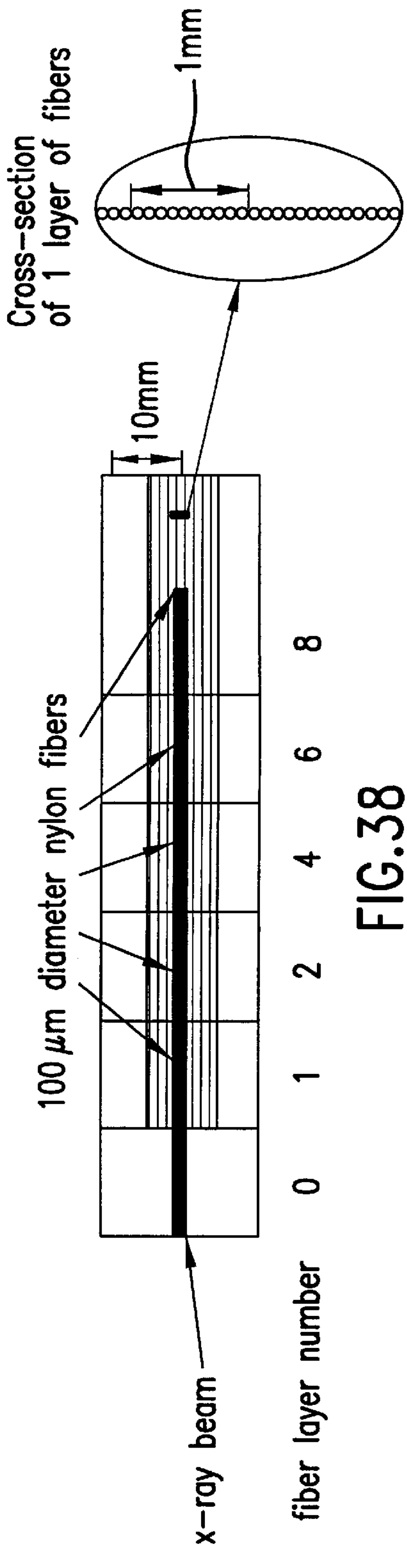
FIG. 38 is a schematic diagram of extinction object comprised of 0.1 mm diameter nylon fibers of various layer thickness: 0, 1, 2, 4, 6 and 8 layers.
Figure 39:
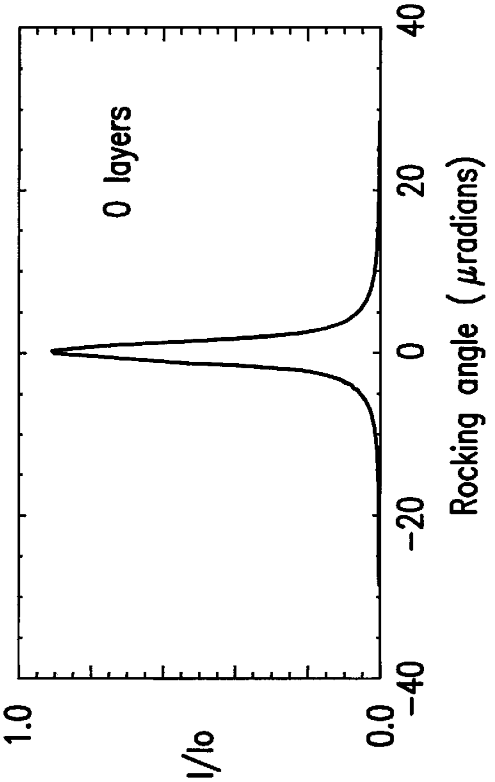
FIG. 39 is a rocking curve obtained at 18 keV in the region of the extinction object where there are no fiber layers (a reference rocking curve).
Figure 40:
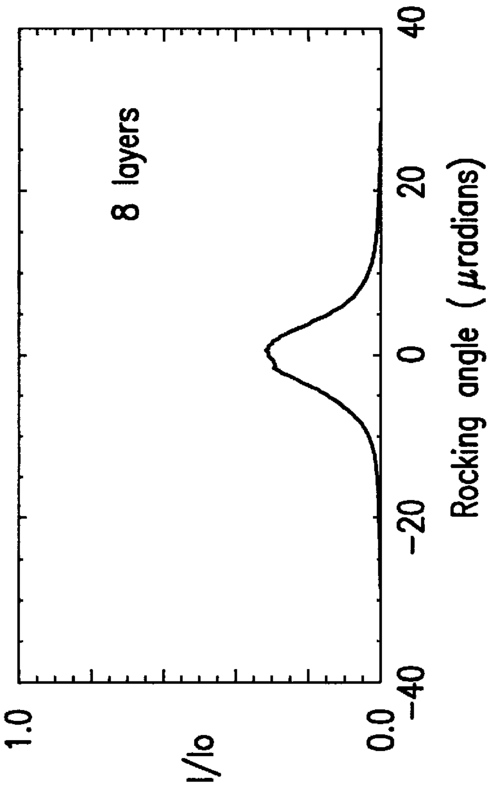
FIG. 40 is a rocking curve obtained at 18 keV in the region of the extinction object where there are 8 fiber layers.
Figure 41:
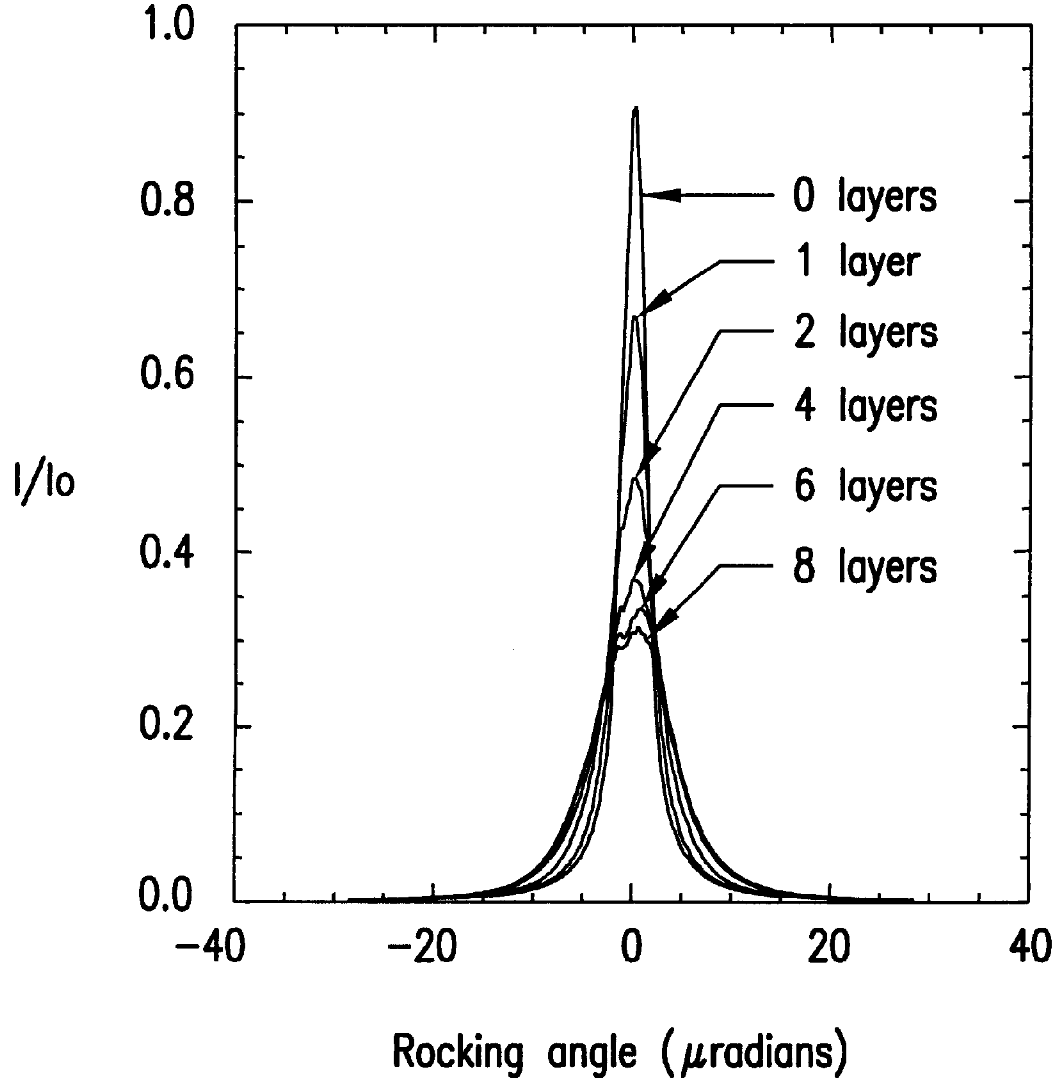
FIG. 41 shows composite rocking curves obtained at 18 keV for 0, 1, 2, 4, 6, and 8 nylon fiber layers. Note the drop in intensity at the peak location and the peak broadening as the fiber layer increases.

An example of an object that has extinction that comprises materials that can be built and tested in a controlled manner is a set of fibers of varying thickness. This object is shown in FIG. 38. It comprises layers of nylon fibers, 0.1 mm thick, tightly wound for form layers of fibers. These fibers are then stacked in layers of 0, 1, 2, 4, 6, and 8 layers as shown. Examples of rocking curves obtained with the 0 and 8 layers were introduced into the DEI system and are shown in FIGS. 39 and 40, respectively. FIG. 41 shows the rocking curves obtained from each of the fiber layers. The intensity loss at the rocking curve peak for each of the layers is given in Table 1.

TABLE 1

| | 0 Layers | 1 Layer | 2 Layers | 4 Layers | 6 Layers | 8 Layers |
|---|---|---|---|---|---|---|
| Percent Peak Intensity Contrast (compared to 0 layer data) | 0.0 | −26.4% | −47.3 | −59.3% | −63.7% | −65.4% |
| Integrated Intensity (microradians) | 3.78 | 3.68 | 3.74 | 3.77 | 3.74 | 3.64 |
| Percent Integrated Intensity Ratio (compared to 0 layer data) | 100% | 97.4% | 99.0% | 99.6% | 99.0% | 96.4% |

This would be the contrast obtained by the presence of the fiber layers in an image compared to the background around the fibers. The integrated intensity (corrected for the measured absorption of the fiber layers) is shown in Table 1. Note that the integrated intensity is within 5% of the no fiber layer showing that the intensity is scattered in angle is not absorbed.

Figure 42:
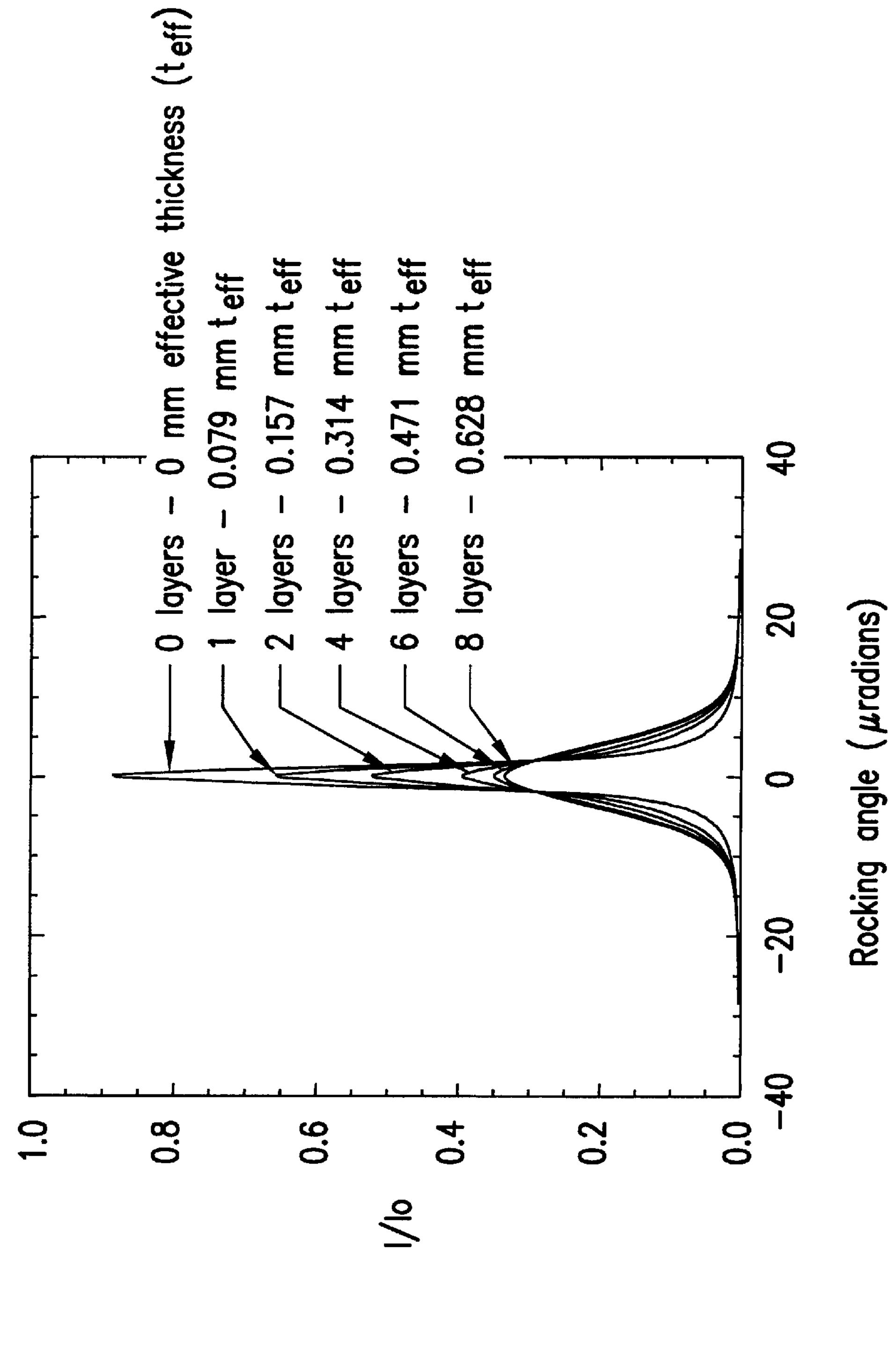
FIG. 42 shows a Gaussian fit to the fiber layer data shown in FIG. 41, wherein the data are fit using the model of Equation 9 with parameters given in the text and the average thickness of the fiber layers shown.

The data were fit to the model of Equation 9. The results of that fit are shown in FIG. 42. The percent error between the fit and the measured data was less than 2% in all cases, the error being measured as the absolute value of difference between the measured and calculated values divided by the measured values at all points in the rocking curve. The extinction value for the fibers at 18 keV was determined to be 67.14 $cm^{-1}$ and the width of the Gaussian distribution was found to be 5.08 microradians.

The contrast obtained by imaging an object between matched perfect crystal sets in a parallel geometry (DEI) can have contributions due to the rejection of ultra-small angle scattering as compared to normal radiography (extinction contrast). The narrow reflection curves of these crystals can reject scatter on an angular scale much smaller than conventional scatter rejection grids. The appearance and apparent importance of this source of contrast has led to detailed measurements and analysis of this contrast. A simple theoretical model accounts for the conversion of direct beam intensity into ultra-small angle scattering described by a Gaussian distribution. This model is compared at two extreme limits of ultra-small angle scattering power represented by a weak small angle scatterer (the ACR tumor simulations) and a fabricated small angle scatterer (a nylon fiber object).

Results indicate that unexpected contrast can be found using the DEI technique according to this invention. In addition to determining independently the refraction contrast of an object, it can exhibit contrast from organized structures within the object.

Since the ability of the DEI system to resolve refraction angles and reject ultra-small angle scattering depends weakly, as opposed to absorption, on the imaging energy, it may be optimally applied higher x-ray energies. This is important in all areas of radiography especially in the case of medical imaging where absorption based radiography must deliver a significant x-ray dose to observe contrast. DEI may be able to observe tissue contrast at high x-ray energies from refraction and or extinction without significant absorption losses (i.e. dose delivery).

DEI is a significant contribution to radiography and current studies are directed to exploring systems of both medical and materials interest.

We claim:

1. In a method for detecting an image of an object, wherein an x-ray beam is generated, the improvement comprising:

transmitting the x-ray beam through a soft tissue material and emitting from the soft tissue material a transmitted beam;

directing the transmitted beam at an angle of incidence upon a crystal analyzer; and detecting an image of the object from only a beam diffracted from the crystal analyzer one of at and near a peak of a rocking curve of the crystal analyzer.

2. In a method according to claim 1 wherein the one of at and near the peak occurs within approximately one-half of a Darwin width of the rocking curve.

3. In a method according to claim 1 wherein the soft tissue material is one of a human body tissue and an animal body tissue.

4. In a method according to claim 1 wherein the soft tissue material is at least one of cartilage, bone, muscle, tendon, ligament, vascular tissue and other connective tissues.

5. In a method according to claim 1 wherein the image is examined to determine one of a normal physiologic state, a structural state and a pathological state.

6. In a method according to claim 1 wherein the image is exposed on a detector.

7. In a method according to claim 6 wherein the detector is capable of producing a digitized image.

8. In a method according to claim 6 wherein the detector is a radiographic film.

9. In a method according to claim 6 wherein the detector is an image plate.

10. In a method according to claim 1 wherein the crystal analyzer upon which the transmitted beams are directed is a Bragg type analyzer.

11. In a method according to claim 1 wherein the transmitted beam has an energy level in a range of approximately 16 keV to approximately 100 keV.

12. In a method according to claim 1 wherein the x-ray beam is diffracted by a monochromator which is matched in orientation and lattice planes to the crystal analyzer.

13. In a method according to claim 1 further comprising increasing a relative intensity of the image of the object by adjusting an angular position of the crystal analyzer.

14. In a method according to claim 13 wherein the angular position of the crystal analyzer is adjusted in steps of approximately 1 microradian increments.

15. In a method according to claim 1 wherein the x-ray beam is a mono-energetic synchrotron beam.

* * * * *

UNITED STATES PATENT AND TRADEMARK OFFICE

CERTIFICATE OF CORRECTION

PATENT NO. : 6,577,708 B2 
DATED : June 10, 2003
INVENTOR(S) : Leroy Dean Chapman et al.

It is certified that error appears in the above-identified patent and that said Letters Patent is hereby corrected as shown below:

Column 1,
Line 3, after the title "DIFFRACTION ENHANCED X-RAY IMAGING OF ARTICULAR CARTILAGE" please insert the following paragraph:
-- This work was supported in part by National Institutes of Health Grant AR 39239, National Institutes of Health Grant GM59395-01, United States Army Medical Research and Material Command Grant DAMD 17-99-1-927, United States Department of Energy DE-AC02-76CH00016, and the State of Illinois Higher Education Cooperative Agreement. --

Signed and Sealed this

Twenty-fourth Day of February, 2004

JON W. DUDAS
*Acting Director of the United States Patent and Trademark Office*

UNITED STATES PATENT AND TRADEMARK OFFICE

CERTIFICATE OF CORRECTION

PATENT NO. : 6,577,708 B2
DATED : June 10, 2003
INVENTOR(S) : Leroy Dean Chapman et al.

It is certified that error appears in the above-identified patent and that said Letters Patent is hereby corrected as shown below:

Column 1,
Line 3, after the Title "DIFFRACTION ENHANCED X-RAY IMAGING OF ARTICULAR CARTILAGE," please delete the paragraph, and in its place insert the following paragraph:

-- This invention was made with Government support under Contract No. DE-AC02-98CH10886 awarded by the Department of Energy. The Government has certain rights in this invention. --

Signed and Sealed this

Twenty-eighth Day of June, 2005

JON W. DUDAS
*Director of the United States Patent and Trademark Office*